United States Patent
McDevitt et al.

(10) Patent No.: US 9,211,307 B2
(45) Date of Patent: Dec. 15, 2015

(54) ACELLULARIZED BIOMATERIAL FROM EMBRYONIC STEM CELLS

(75) Inventors: Todd Christopher McDevitt, Atlanta, GA (US); Rehka Ramachandran Nair, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1030 days.

(21) Appl. No.: 12/092,863

(22) PCT Filed: Nov. 8, 2006

(86) PCT No.: PCT/US2006/043711
§ 371 (c)(1),
(2), (4) Date: May 7, 2008

(87) PCT Pub. No.: WO2007/056547
PCT Pub. Date: May 18, 2007

(65) Prior Publication Data
US 2008/0254092 A1    Oct. 16, 2008

Related U.S. Application Data

(60) Provisional application No. 60/734,584, filed on Nov. 8, 2005.

(51) Int. Cl.
*A61K 35/34*    (2015.01)
*A61K 35/54*    (2015.01)
*A61K 35/545*   (2015.01)

(52) U.S. Cl.
CPC ............... *A61K 35/34* (2013.01); *A61K 35/545* (2013.01)

(58) Field of Classification Search
CPC ............................ A61K 35/34; A61K 35/545
See application file for complete search history.

(56) References Cited

U.S. PATENT DOCUMENTS

| | | | |
|---|---|---|---|
| 6,448,076 B2 | 9/2002 | Dennis et al. | |
| 2002/0115208 A1 | 8/2002 | Mitchell et al. | |
| 2003/0148510 A1 | 8/2003 | Mitrani | |
| 2005/0013870 A1* | 1/2005 | Freyman et al. | 424/520 |
| 2005/0013872 A1 | 1/2005 | Freyman | |
| 2005/0043819 A1 | 2/2005 | Schmidt et al. | |
| 2005/0153442 A1 | 7/2005 | Katz et al. | |
| 2005/0256588 A1* | 11/2005 | Sawa et al. | 623/23.72 |
| 2006/0104958 A1 | 5/2006 | Akins et al. | |

FOREIGN PATENT DOCUMENTS

| | | |
|---|---|---|
| WO | WO 0240630 A2 * | 5/2002 |
| WO | WO 2005/009497 | 2/2005 |
| WO | WO 2005/009498 | 2/2005 |
| WO | WO 2007/011693 | 1/2007 |

OTHER PUBLICATIONS

Zeltinger et al. Tissue Engineering, 7(1): 9-22, 2001.*
Gerecht-Nir et al. Laboratory Investigation, 83(12): 1811-1820, 2003.*
Strategene catalog, 1988, p. 39, Gene Characterization Kits.*
Stem Cells: Scientific Progress and Future Research Directions, Appendix F, "embryoid body", accessed online at http://stemcells.nih.gov/info/2001report/2001report, Apr. 13, 2010.*
Alperin, et al., "Polyurethane films seeded with embryonic stem cell-derived cardiomyocytes for use in cardiac tissue engineering applications", *Biomaterials*, 26(35):7377-86 (2005).
Assmus, et al., "Transplantation of Progenitor Cells and Regeneration Enhancement in Acute Myocardial Infarction (Topcare-AMI)", *Circulation*, 106(24):3009.17 (2002).
Badylak, et al., "Extracellular matrix for myocardial repair", *Heart Surg. Forum*, 6(2):E20-6 (2003).
Becker and Hart, "Reorganization of filamentous actin and myosin-II in zebrafish eggs correlates temporally and spatially with cortical granule exocytosis", *J. Cell Sci*, 112 ( Pt 1):97.110 (1999).
Behfar, et al., "Stem cell differentiation requires a paracrine pathway in the heart", *FASEB J.*, 16(12):1558-66 (2002).
Chen and Kosco, "Differentiation of mouse embryonic stem cells in vitro: III. Morphological evaluation of tissues developed after implantation of differentiated mouse embryoid bodies.", *Dev. Dyn.*, 197(3):217-26 (1993).
Christman, et al., "Injectable fibrin scaffold improves cell transplant survival, reduces infarct expansion, and induces neovasculature formation in ischemic myocardium", *J. Am. Coll. Cardiol.*, 44(3):654-60 (2004).
Czyz and Wobus, "Embryonic stem cell differentiation: the role of extracellular factors", *Differentiation*, 68(4-5):167.74 (2001).
Davis, et al., "Injectable self-assembling peptide nanofibers create intramyocardial microenvironments for endothelial cells", *Circulation*, 111(4):442-50 (2005).
Desbaillets, et al., "Embryoid bodies: an in vitro model of mouse embryogenesis", *Exp. Physiol.*, 85(6):645-51 (2000).
Dib, et al., "Feasibility and safety of autologous myoblast transplantation in patients with ischemic cardiomyopathy", *Cell Transp$^{lant.}$*, 14(1):11.9 (2005).
Fraidenraich, et al., "Rescue of cardiac defects in id knockout embryos by injection of embryonic stem cells", *Science*, 306(5694):247-52 (2004).
Kim, et al., "Fluorometric assay of DNA in cartilage explants using Hoechst 33258", *Anal. Biochem.*, 174(1):168-76 (1988).
Klug, et al., "Genetically selected cardiomyocytes from differentiating embronic stem cells form stable intracardiac grafts", *J. Clin. Invest.*, 98(1):216-24 (1996).
Kofidis, et al., "Injectable bioartificial myocardial tissue for large-scale intramural cell transfer and functional recovery of injured heart muscle", *J. Thorac. Cardiovasc. Surg.*, 128(4):571-8 (2004).

(Continued)

*Primary Examiner* — Thaian N Ton
(74) *Attorney, Agent, or Firm* — Pabst Patent Group LLP (57) ABSTRACT

Compositions containing acellularized biomaterial derived from differentiating pluripotent cells, for example, embryonic stem cells are provided. The acellularized biomaterial can be used to promote wound healing, promote tissue regeneration, or inhibit scarring. Methods for using the acellularized biomaterial for treating degenerative diseases are also provided.

12 Claims, 6 Drawing Sheets

(56) References Cited

OTHER PUBLICATIONS

Kofidis, et al., "Myocardial restoration with embryonic stem cell bioartificial tissue transplantation", *J. Heart Lung Transplant.*, 24(6):737-44 (2005).

Menasche, et al., "Autologous skeletal myoblast transplantation for severe postinfarction left ventricular dysfunction", *J. Am. Coll. Cardiol.*, 41(7):1078-83 (2003).

Min, et al., "Long-term improvement of cardiac function in rats after infarction by transplantation of embryonic stem cells",*J. Thorac. Cardiovasc. Surg.*, 125(2):361-9 (2003).

Min, et al., "Transplantation of embryonic stem cells improves cardiac function in postinfarcted rats", *J. Appl. Physiol.*, 92(1):288-96 (2002).

Pagani, et al., "Autologous skeletal myoblasts transplanted to ischemia-damaged myocardium in humans. Histological analysis of cell survival and differentiation.", *J. Am. Coll. Cardiol.*, 41(5):879-88 (2003).

Perin, et al., "Transendocardial, autologous bone marrow cell transplantation for severe, chronic ischemic heart failure", *Circulation*, 107(18):2294-302 (2003).

Robinson, et al., "Extracellular matrix scaffold for cardiac repair", *Circulation*, 112:1.135-1.143 (2005).

Rodda, et al., "Embryonic stem cell differentiation and the analysis of mammalian development", *Int. J. Dev. Biol.*, 46(4):449-58 (2002).

Rudy-Reil & Lough, "Avian precardiac endodermlmesoderm induces cardiac myocyte differentiation in murine embryonic stem cells", *Circulation Research*, 94(12):1638:107-116 (2004).

Strauer, et al., "Repair of infarcted myocardium by autologous intracoronary mononuclear bone marrow cell transplantation in humans", *Circulation*, 106(15):1913-8 (2002).

Toma, et al., "Human mesenchymal stem cells differentiate to a cardiomyocyte phenotype in the adult murine heart", *Circulation*, 105(1):93-8 (2002).

Tomita, et al., "Autologous transplantation of bone marrow cells improves damaged heart function", *Circulation*, 100(19 Suppl):II247-56 (1999).

Vandervelde, at al., "Signaling factors in stem cell-mediated repair of infarcted myocardium", *Mol. Cell. Cardiol.*, 39(2):363-76 (2005).

Zimmermann, et al., "Cardiac grafting of engineered heart tissue in syngenic rats", *Circulation*, 106(12 Suppl 1):I151-7 (2002).

Chan.G, et al., "Embryonic cortical stem cells secrete diffusible factors to enhance their survival," *Neuroreport*, 14(9): 1191-5 (2003).

Croizat, et al., "Embryonic stem cells release potentially novel hematopoietic factors," *Acta Haematologica*, 102(4): 172-179 (1999).

Nair, et al., "Acellular matrices derived from differentiating embryonic stem cells," *J. Biomed. Mat. Res. A.*, 87(4):1075-85 (2008).

Nair, et al., "Efficiency of solvent extraction methods for acellularization of embryoid bodies," *Journal of Biomaterials Science Polymer Edition*, 19(6): 801-19 (2008).

Schultheiss, et al, "Biological vascularized matrix for bladder tissue engineering: matrix preparation, reseeding technique, and short-term implantation in a porcine model," *J. Urology*, 173(1): 276-80 (2005).

\* cited by examiner

ACELLULARIZED BIOMATERIAL FROM EMBRYONIC STEM CELLS

RELATED APPLICATION

This application is a filing under 35 U.S.C. §371 of PCT/US2006/043711 filed with the U.S. Receiving Office of the Patent Cooperation Treaty on Nov. 8, 2006, and claims benefit of and priority to U.S. Provisional Patent Application No. 60/734,584 filed on Nov. 8, 2005, and where permissible is incorporated by reference herein in its entirety.

GOVERNMENT SUPPORT

Aspects of the work disclosed herein were supported, in part, by Grant No. EEC-9731643 awarded by the National Science Foundation. Accordingly, the U.S. government has certain rights in the claimed subject matter.

FIELD OF THE INVENTION

Aspects of the invention are generally directed to acellularized biomaterial compositions, in particular acellularized biomaterial compositions derived from embryonic stem cells.

BACKGROUND OF THE INVENTION

A number of different stem cells, including embryonic, bone marrow and cardiac progenitors, are currently being examined as potential therapies to repair injured tissues, for example myocardium. These approaches typically focus on regenerating cellularity and restoring tissue function. Thus far, independent of the particular cell type, stem cell therapies have consistently demonstrated enhancements in tissue function in experimental models and clinical trials. However, the precise mechanisms responsible for global functional improvements have yet to be fully elucidated since improvements can be detected even in the absence of any substantial amount of regenerated tissue. This suggests that even if stem cells capable of differentiating into specific cell types are delivered to a damaged tissue, intrinsic signals capable of directing tissue specific differentiation may be absent or deficient within the microenvironment of the damaged tissue.

To date, biomaterials utilized in tissue restoration therapies have largely served a structural role as either a delivery vehicle for tissue and tissue engineering or as a patch for tissue defects. Despite the clear therapeutic potential of stem cells, several drawbacks, including the potential immunogenicity and tumorigenicity of the cells in vivo still exist.

The extracellular matrix (ECM), largely composed of adhesive proteins, cytokines and polysaccharides, constitutes the biochemical and mechanical nature of the microenvironment that regulates cell fate and function within tissues. Curiously, very little is known about the complex assembly of the ECM present during early cell and tissue development though these molecules are thought to provide critical cues that instruct cell behavior. Pluripotent ES cells provide an in vitro model of development and are currently being examined in a number of experimental models as a potential cell therapy to regenerate diseased or injured tissues. However, thus far, no studies have examined the role of the extracellular matrix contributed by ES cells to tissue repair processes.

It is an object of the present invention to provide acellularized biomaterial derived from pluripotent cells, for example embryonic stem cells.

It is also an object of the present invention to provide methods and compositions that promote wound healing, promote tissue regeneration, or reduce scarring.

SUMMARY OF THE INVENTION

Aspects of the disclosure provide acellularized biomaterial derived from pluripotent cells, for example differentiating stem cells. Certain aspects provide acellularized biomaterial derived from differentiating embryonic stem cells (ESC). Acellularized tissues have been examined before in various wound healing models, but the tissue source for the acellular biomaterial was never derived from an embryonic source actively undergoing differentiation for example, morphogenesis. Moreover, existing stem cell therapies are based on the administration of stem cells which differentiate in vivo to regenerate damaged or missing tissue. Aspects of the disclosure are based on the principle that biomolecules synthesized by stem cells may be as important, if not more so, than functional differentiation of the cells. Thus, the application of stem cells themselves is not as important as the application of biomolecules produced by stem cells. This represents a fundamental paradigm shift in stem cell regenerative therapies. It is believed that the disclosed acellularized biomaterial provides a complex of molecules with potent regenerative abilities in adult wound healing environments. The acellularized biomaterial also provides a system to deliver embryonic molecular morphogenic cues directly to adult tissues.

Other aspects provide methods of treating a degenerative disease by administering the acellularized biomaterial derived from differentiating embryonic stem cells in an amount effective to promote healing or tissue regeneration. The acellularized biomaterial can be administered in combination or alternation with pluripotent cells or other cell types. A particular aspect provides a method for treating a cardiac disorder by administering acellularized biomaterial derived from differentiating embryonic stem cells in an amount effective to promote healing or tissue regeneration.

Another aspect provides a method to reduce or inhibit scar formation in host by administering acellularized biomaterial derived from differentiating pluripotent cells to the wound or damaged tissue.

Still another aspect provides a medical device, for example a stent at least partially coated with acellularized biomaterial derived from differentiating pluripotent cells.

DETAILED DESCRIPTION OF THE INVENTION

I. Definitions

The term "acellularized biomaterial" refers to material produced from a living organism that no longer contains living cells.

The term "adult tissue" refers to tissue from an organism that has completed gestation. In certain embodiments, adult tissue does not include fetal or embryonic tissue.

The term "cardiac differentiation" refers to totipotent or pluripotent cells undergoing developmental events leading to the acquisition of one or more characteristics of a cardiac cells and/or tissue.

The term "control" refers to an experiment performed without the active ingredient, for example without acellularized biomaterial. Controls are known in the art.

The term "disease" refers to a disordered or incorrectly functioning organ, tissue, structure, or system of the body of an organism resulting from the effect of genetic or developmental errors, infection, poisons, nutritional deficiency or imbalance, toxicity, or unfavorable environmental factors.

The term "embryonic stem cell" refers to cells derived from the inner cell mass of a developing blastocyst, for example a mouse or human blastocyst, and are known to be "pluripotent", meaning that they can differentiate into any somatic cell type.

The term "epidermal differentiation" refers to the differentiation of a pluripotent or totipotent cell into an epidermal cell type such that the totipotent or pluripotent cell acquires one or more characteristics of an epidermal cell type.

The term "heterologous nucleic acid" refers to a nucleic acid derived from another organism.

The term "myogenic differentiation" refers to the differentiation of a pluripotent or totipotent cell into a mesodermal cell type such that the totipotent or pluripotent cell acquires one or more characteristics of a mesodermal cell type The term "neural differentiation" refers to the differentiation of a pluripotent or totipotent cell into a neural cell type such that the totipotent or pluripotent cell acquires one or more characteristics of a neural cell type.

The term "paracrine factor" refers to a substance secreted by an embryonic stem cell that acts on adjacent cells. Representative paracrine factors include, but are not limited to growth factors, mitogens, cytokines, developmental factors or cues, or combinations thereof.

The term "regenerative tissue repair" refers to repair of damaged tissue by inducing cells of the damaged tissue to replace the damaged cells or tissue.

The term "wound" refers to damage to a tissue or organ and can be external or internal.

II. Compositions

One embodiment provides acellularized biomaterial derived from pluripotent cells such as embryonic stem cells undergoing differentiation, for example in vitro. Differentiation includes morphogenesis. Morphogenesis refers to differentiation of cells and tissues in the early embryo which results in establishing the form and structure of the various organs and parts of the organism's body. The acellularized biomaterial can be functionally capable of inducing or facilitating wound healing including regenerative tissue repair in vitro or in vivo. The acellularized material can also contain extracellular material, optionally in combination with paracrine factors produced by the embryonic stem cells. Typically the acellularized material contains paracrine factors produced by the pluripotent cells, such as embryonic stem cells, as the cells differentiate in vitro, for example into a specific tissue type.

Embryonic stem cells can differentiate into any cell type, for example, epidermal, mesodermal, or endodermal cell types or tissues. Thus, acellularized material can be produce that is specific for epidermal, mesodermal, or endodermal derived tissues or wounds in specific tissues.

Exemplary specific tissues include, but are not limited to cardiac, bone, skin, skeletal muscle, smooth muscle, arterial tissue, ocular tissue, neural tissue, skin tissue, liver tissue, pancreatic tissue, insulin-producing tissue, or combinations thereof.

The paracrine factors can be linked, conjugated, or covalently bound to the extracellular material. In certain embodiments, the paracrine factors can diffuse out of the acellularized biomaterial and into the wound or damaged tissue. The diffusion of the paracrine factors can produce a gradient of one or more paracrine factors across a section of the wound or damaged tissue. Additionally, the acellularized biomaterial can function as a controlled release device for the controlled, sustained delivery of stem cell paracrine factors.

In other embodiments, the acellularized material physically interacts with the wound or damaged tissue to promote healing. The healing can result from the physical interaction alone or in combination with paracrine factors released from the acellularized biomaterial.

Another embodiment provides acellularized biomaterial derived from embryonic stem cells having inherent regenerative properties for tissue restoration and wound repair can be used independently or in conjunction with cell therapies.

It is believed that the disclosed acellularized biomaterial advantageously promotes, facilitates, or induces wound healing, including but not limited to regenerative tissue repair, by altering the microenvironment of the wound or damaged tissue to more closely resemble the microenvironment of developing tissue, for example embryonic tissue. The acellularized biomaterial alters the microenvironment of the wound by physically interacting with cells of the wound or tissue and optionally by delivering stem cell paracrine factors to cells in and around the wound in amounts, concentrations, and durations effective to cause the cells in the wound or damaged tissue to participate in the healing process. Thus, unlike existing stem cell therapies that attempt to add stem cells and have the stem cells reproduce to form tissue, it is believed that the disclosed acellularized material causes existing cells in the wound or damage tissue to undergo biological changes that promote healing.

The components of the acellularized biomaterial are described more fully below.

A. Embryonic Stem Cell Biomaterial

1. Embryonic Stem Cells

The disclosed acellularized biomaterial is produced by pluripotent cells or stem cells, preferably embryonic stem cells. The embryonic stem cells can be mammalian. In other embodiments, the stem cells can be non-human stem cells or chimeric stem cells produced, for example, from a human and a non-human mammal. It will be appreciated that any stem cell producing one or more extracellular matrix components and paracrine factors can be utilized to produce the disclosed acellularized biomaterial. Embryonic stem (ES) cells are derived from the inner cell mass of a developing blastocyst, for example mouse, human, or non-human blastocyst, and are known to be "pluripotent", meaning that they can differentiate into any somatic cell type. Their ability to differentiate into cell types, such as cardiomyocytes, neurons and hepatocytes, in vitro and in vivo, suggests they could be applicable to a number of degenerative cellular disorders in which endogenous mechanisms of cell replacement fail to adequately regenerate tissues. ES cells are typically cultured in Petri dishes on a layer of feeder cells or on a matrix-coated substrate and supplemented with soluble factors to stimulate cell growth in an "undifferentiated" state. In order to initiate differentiation, the adherent ES cells are displaced from the surface and placed in suspension culture, whereupon they form aggregates of cells referred to as embryoid bodies (EBs). Individual EBs recapitulate most of the molecular signaling and cell differentiation events of embryonic post-implantation tissues, including differentiation of the cells into the three germ lineages (ectoderm, endoderm and mesoderm) from which all other progenitor cells and subsequent somatic cells are formed. Molecular environments within EBs regulate the course of cellular differentiation that ensues. Thus, another embodiment provides acellularized biomaterial derived from mammalian embryoid bodies, including but not limited to non-human embryoid bodies, differentiating in vitro.

2. Extracellular Matrix Material

The disclosed acellularized biomaterials include one or more extracellular matrix (ECM) components, for example, structural components, functional components, or a combination thereof. The ECM is widely known to have both structural and functional components responsible for maintaining normal tissue homeostasis and the ECM undergoes dynamic changes in response to perturbations, such as cell or tissue injury, or the onset of degenerative disease. Much less is known about the roles of the ECM in morphogenic events, such as during developmental biology and tissue regeneration, perhaps due to lack of a suitable mammalian model, particularly for regeneration.

Two primary components of the ECM are proteins and polysaccharides (i.e., glycosaminoglycans (GAGs)). ECM proteins, such as collagen I and IV, fibronectin, and laminin play structural and functional roles in the maintenance of tissues. Collagen I is typically the most abundant protein in the ECM of adult tissues, however, over 20 different types of collagen have been discovered, each with their own function. Collagen IV, for example, is present in the basement membrane of vascular structures and serves as a ligand for endothelial cells. Fibronectin is both a structural and functional protein, as it is a ligand for several different cell types. Laminin is yet another protein prevalent in the basement membrane and has been found to play a role in vascular structure maintenance. Growth factors, such as fibroblast growth factor (FGF), hepatocyte growth factor (HGF), platelet-derived growth factor (PDGF), vascular endothelial cell growth factor (VEGF), and insulin-like growth factor (IGF), can bind directly to ECM proteins or via proteoglycans or GAGs and be stably retained in a bound state within the ECM. Most of these growth factors also come in several distinct isoforms that can affect cells in different manners depending on associated biochemical elements within the context of the matrix. A number of GAGs, including chondroitin sulfate, heparin sulfate, and hyaluronic acid, and proteoglycans, such as perlecan, versican, and decorin are also often present in the ECM. GAGs and proteoglycans have multiple functions in the ECM, including binding growth factors. Potent morphogenic molecules like WNTs and bone morphogenic proteins (BMP), as well as their antagonists, such as noggin and chordin for BMPs, can also be found in the ECM. The nucleic acid and amino acid sequences for the genes and proteins discussed above are known in the art and can be found, for example in GENBANK.

In addition to the homeostatic role of the ECM in tissue maintenance, the dynamic nature of the ECM in response to tissue injury or disease can significantly influence the course and outcome of wound healing and regeneration. Specifically, fibronectin has been found to be an important molecule for normal tissue morphogenesis and regeneration. Another component found to be important for morphogenesis is the basement membrane protein, laminin. Hyaluronic acid (HA) is yet another molecule of potential regenerative interest and has a role in binding growth factors and cytokines and promoting water retention. It has been considered for induction of regenerative events in the past due to its high concentration in newborn and fetal tissue as well as its involvement in cell migration and wound repair processes.

Additionally, several WNT proteins have been identified to play a critical role in limb regeneration in lower organisms and bone growth in mammals. As their name implies, BMP proteins are essential components of the normal bone formation and inhibition of the BMP pathway has been found to have a significant effect on regeneration events. The combination and concentration of ECM proteins and paracrine factors can be adjusted depending on the type of tissue needing repair.

B. Cellular Therapy

The disclosed acellularized biomaterial can optionally be used in combination or alternation with cellular therapies. Thus, the biomaterial can be seeded with one or more cells or types of cells to promote or facilitate healing. The seeding can occur before or after the acellularized biomaterial is delivered to the wound or damaged tissue. The types of cells used to seed the biomaterial can be selected based on the type of wound or damaged tissue to be treated. Generally, pluripotent cells can be used to seed the biomaterial so that the seeded cells and the biomaterial interact synergistically to promote healing. In one embodiment, the pluripotent cells thereof respond in vivo to the acellularized biomaterial and the paracrine factors associated with the acellularized biomaterial and differentiate into a predetermined cell type or tissue. It will be appreciated that other cell types, including but not limited to stem cells, somatic cells, or a combination thereof can be used in combination with the acellularized material.

For example, acellularized biomaterial specific for cardiac material can be obtained from embryonic stem cells by culturing the embryonic stem cells under conditions and a duration that induce the embryonic stem cells to differentiate into cardiac or cardiac-like material. The biomaterial can be acellularized, and optionally stored. The biomaterial can then be combined with cells prior or subsequent to delivering the biomaterial to the wound or damaged tissue, for example cardiac tissue.

1. Pluripotent or Totipotent Cells

Representative cells that can be used in combination with the acellularized biomaterial derived from embryonic stem cells include, but are not limited to, mammalian, human, or non-human embryonic or adult stem cells; pluripotent or totipotent cells obtained from placenta, cord blood, adipose tissue, neural tissue, muscle tissue, cardiac tissue, epidermal tissue, or bone marrow; autologous cells, heterologous cells, or somatic cells optionally corresponding to the tissue to be treated.

2. Recombinant Cells

The cells used in combination with the disclosed acellularized biomaterial can be recombinant cells that express one or more heterologous nucleic acids. The heterologous nucleic acid can express a protein involved in wound healing or tissue regeneration, for example an extracellular matrix protein, matrix metalloprotease or GAG synthase, or a fusion protein thereof. Alternatively, the cell can be genetically engineered to secrete embryonic stem cell paracrine factors including, but not limited to growth factors such as fibroblast growth factor, hepatocyte growth factor, platelet-derived growth factor, vascular endothelial cell growth factor, and insulin-like growth factor, bone morphogenic proteins and combinations thereof. Methods and protocols for producing recombinant cells are known in the art.

C. Pharmaceutical Compositions

Another embodiment provides pharmaceutical compositions and dosage forms including the disclosed acellularized biomaterial. Pharmaceutical unit dosage forms of the compounds of this disclosure are suitable for mucosal (e.g., nasal, sublingual, vaginal, buccal, or rectal), parenteral (e.g., intramuscular, subcutaneous, intravenous, intra-arterial, or bolus injection), or topical administration to a patient. Examples of dosage forms include, but are not limited to: dispersions; ointments; cataplasms (poultices); pastes; powders; dressings; creams; plasters; solutions; patches; gels; and sterile solids suitable for parenteral administration to a patient.

The composition, shape, and type of dosage forms of the compositions of the disclosure will typically vary depending on their use. These and other ways in which specific dosage forms encompassed by this disclosure will vary from one another will be readily apparent to those skilled in the art. See, e.g., Remington's Pharmaceutical Sciences, 18th ed., Mack Publishing, Easton, Pa. (1990).

Pharmaceutical compositions and unit dosage forms of the disclosure typically also include one or more pharmaceutically acceptable excipients or diluents. Advantages provided by specific compounds of the disclosure, such as, but not limited to, increased solubility and/or enhanced flow, purity, or stability (e.g., hygroscopicity) characteristics can make them better suited for pharmaceutical formulation and/or administration to patients than the prior art. Suitable excipients are well known to those skilled in the art of pharmacy or pharmaceutics, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient.

The disclosure further encompasses pharmaceutical compositions and dosage forms that include one or more compounds that reduce the rate by which the acellularized biomaterial will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate or organic acids. A specific solubility modulator is tartaric acid.

Like the amounts and types of excipients, the amounts or acellularized biomaterial in a dosage form may differ depending on factors such as, but not limited to, the route by which it is to be administered to patients. However, typical dosage forms of the compounds of the disclosure are in an amount of from about 10 mg to about 1000 mg, preferably in an amount of from about 25 mg to about 750 mg, more preferably in an amount of from 50 mg to 500 mg, even more preferably in an amount of from about 30 mg to about 100 mg.

Representative excipients include, but are not limited to, water, acetone, ethanol, ethylene glycol, propylene glycol, butane-1,3-diol, isopropyl myristate, isopropyl palmitate, mineral oil, gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars and starches and mixtures thereof.

Depending on the specific tissue to be treated, additional components may be used prior to, in conjunction with, or subsequent to treatment with acellularized biomaterial of the disclosure. For example, protease inhibitors and other compounds that prevent the degradation of the acellularized material can be used.

D. Combination Therapy

The acellularized biomaterial derived from embryonic stem cells can be used in combination with a second therapeutic agent to facilitate healing and optionally, reduce or inhibit scarring. Suitable therapeutic agents include but are not limited to antibiotics, antioxidants, anti-viral agents, anti-inflammatory agents, cytokines, and growth factors such as fibroblast growth factor, hepatocyte growth factor, platelet-derived growth factor, vascular endothelial cell growth factor, and insulin-like growth factor. The amount of a second therapeutic generally depends on the tissue to be treated. Specific dosages can be readily determined by those of skill in the art. See Ansel, Howard C. et al. *Pharmaceutical Dosage Forms and Drug Delivery Systems* ($6^{th}$ ed.) Williams and Wilkins, Malvern, Pa. (1995). Alternatively, the acellularized biomaterial can be used in combination with cell delivery, for example, the delivery of stem cells, pluripotent cells, somatic cells, or combinations thereof.

III. Methods of Making Acellularized Biomaterials

The disclosed biomaterial is obtained from cultured pluripotent cells such as stem cells undergoing differentiation or morphogenesis. A preferred method uses embryonic stem cells; however, it will be appreciated that any pluripotent cell can be used provided the cell can be induced to differentiate, for example into a specific cell or tissue or can develop at least one or more characteristics of a specific cell type or tissue type. The stem cells are induced to differentiate and typically form aggregates known as embryoid bodies. Conditions and growth factors for inducing stem cells to differentiate or produce specific cell types or tissues are known in the art. The embryoid bodies can be harvested at different time periods depending the type of cells or tissue to be treated. After the embryonic stem cells have differentiated, the biomaterial is harvested and acellularized.

Acellularization is the process of removing cells from a tissue without disrupting the native structure and composition of its ECM. Examples of tissues that have been acellularized include porcine intestinal collagen layer, skin, bladder, human placenta, liver, and blood vessels, with applications varying from heart valves to nerve grafts. Some of the tissues are used to regenerate the same tissue, whereas others are used in different sites, such as SIS for tendon/ligament repair or myocardial healing. Acellularization has been used to create a number of different natural biomaterials since their ECM-based composition, largely conserved across species, is less likely to elicit an immune response. The wide range of these tissues that can be acellularized suggests the need for a variety of acellularization processes. Common protocols generally involve both physical and chemical means of disrupting cellular structure and removing their contents. Physical methods can involve freeze-thaw, pressure, and sonication techniques. General mechanical agitation has also been used, though optimal cellular removal combines physical disruption with chemical extraction treatments.

The variety of chemical procedures that have been used to acellularize different tissue samples can be categorized into alkaline or acid treatments, non-ionic or ionic detergents, and enzymatic treatments. Acid/alkaline treatments include acetic acid, peracetic acid (PAA), and ammonium hydroxide, and are used to solubilize cellular cytoplasmic components and disrupt nucleic acids. PAA in particular has been found to be effective at removing cellular material while maintaining ECM components of thin tissues and serving as a disinfectant. Specifically, ECM proteins, GAGs, and growth factors are stably retained post-treatment. Ionic detergents have been used for solubilization of nuclear and cytoplasmic membranes. Sodium dodecyl sulfate (SDS) in particular has been widely incorporated into acellularization protocols and was found to remove nuclear content, although it tended to significantly disrupt ECM components. Non-ionic detergents, which disrupt lipid-lipid and lipid-protein interactions, are often used to lyse cellular membranes and offer a more gentle treatment. One of the most common detergents used is Triton X-100, although some studies have shown variable success in its ability to remove cellular material. Similarly, conflicting reports exist on the maintenance of ECM components after Triton X-100 treatment, where in some cases, use of the reagent removed all GAG content, while in other cases an insignificant difference in GAG and collagen components was observed. Finally, enzymatic treatments such as trypsin and DNase have been used to either cleave peptide bonds or digest nucleotides. Conflicting reports on the varying successes of similar acellularization treatments on different tissues lends support to the notion that different reagents must be optimized for each tissue by controlling the concentrations and durations of treatments significant effects on the acellularized product.

A preferred method for acellularizing biomaterial produced by embryonic stem cells includes treating the biomaterial with a combination of a detergent and DNAase as described in Example 1. An exemplary method provides treating embryoid bodies with 0.1 to 1% (w/v) of detergent, for example a nonionic detergent, and 1 mg/ml DNase for about 30 minutes. The biomaterial to be acellularized can be allowed to differentiate in vitro for any length of time, for example, about 1 hr to about 12 hrs, or 1, 2, 3, 4, 5, 6, 7, 8, 9, 10, 11, 12, 13, 14, or more days.

IV. Methods of Use

A. Wound Healing

The disclosed acellularized biomaterial is useful for promoting or inducing wound healing in adult tissue, in particular cardiac or neural wound healing. The acellularized biomaterial can be delivered to a wound or damaged tissue, for example tissue that has lost the capacity to regenerate on its own.

Mammalian adult myocardium lacks inherent regenerative capacity since mature cardiomyocytes exhibit a limited ability to proliferate in response to injury. Thus, following an incidence of ischemia, infarcted myocardial tissue fails to regenerate properly and the normal wound healing process results in the formation of a permanent, fibrotic scar. Scar formation, instead of tissue regeneration, initiates a series of deleterious ventricular remodeling events that eventually lead to cardiac failure and mortality. Modulating and preventing scar tissue formation in the wounded heart could serve to 1) prevent adverse ventricular remodeling and 2) improve global cardiac function. Modulating the molecular composition of infarcted myocardial tissue to favor cardiomyogenic differentiation provides a more conducive environment for cellular regeneration of the myocardial tissue by endogenous and optionally exogenous stem cell therapies. Thus, one embodiment provides a method for treating a cardiac disease or disorder by administering acellularized biomaterial derived from embryonic stem cells to damaged or wounded cardiac tissue in an amount effective to heal or regenerate damaged cardiac tissue.

The wound can be external or internal. Typically, the acellularized biomaterial is placed in contact with the wound so that the acellularized biomaterial physically interacts with cells of the wound or damaged tissue. If the wound is internal, the acellularized material can be administered surgically, or can be administered using a medical device adapted for delivering compounds internally, for example to the heart or other organ.

B. Inhibition of Scarring

The disclosed acellularized biomaterials can also be used to reduce scarring. It is believed that the embryonic environment prevents scar formation, permits tissue regeneration, and is distinctly different from that of an adult. Scar tissue formation is a common adverse response exhibited by most adult mammalian species as a result of acute injury or chronic diseases resulting in abnormal tissue structure. Typically, pluripotent embryonic stem cells are used as a robust cell source for the treatment of various degenerative diseases that cause irreplaceable endogenous cell loss. It has been discovered that the disclosed acellularized biomaterials derived from embryonic stem cells can be used to mimic the embryonic microenvironment in adult tissues and reduce scarring.

During the early stages of development, mammalian fetuses possess the ability to heal injuries in a scar-free manner, whereas a permanent transition occurs later during gestation whereby tissue injury results in scar formation rather than tissue regeneration. The curious ability of fetuses to heal wounds has long baffled scientists, but has also provided model systems to identify and characterize the role of various molecules that either stimulate or antagonize proper wound healing rather than scar tissue formation. Similar regeneration capabilities have also been described in other systems, specifically newts and the MRL strain of mice. Scarless wound healing is desirable because the excessive ECM reorganization associated with scarring results in compromised tissue function and decreased mechanical strength of the injured area. Additionally, hallmarks of fetal repair involve hair follicle and sebaceous gland regeneration. The skin wound healing model has long been recognized as the most relevant system for studying scarless regeneration in fetuses and adults. Accordingly, a number of different models have been created to examine the mechanisms of wound repair of the skin, such as excisional, incisional and burn wounds. Each of these models have distinct advantages and disadvantages compared to the others, but the excisional wound model provides an easily reproducible wound that can be tracked visually during the time course of healing and is amenable to a number of quantitative measures of tissue repair, such as wound closure rate, reepithelialization rate and thickness, and the density of cell invasion by macrophages and blood vessels.

One embodiment provides acellularized biomaterial derived from differentiating embryonic stem cells that is capable of reducing scar formation in a wound or damaged tissue. It is believed that the acellularized biomaterial mimics in adult tissues, at least in part, the embryonic microenvironment. The acellularized biomaterial can be placed in contact with a wound or damaged tissue. The acellularized biomaterial can then physically interact with the wound or damaged tissue to stimulate existing cells to heal with little or no scar formation relative to a control. Alternatively, paracrine factors associated with the acellularized biomaterial can stimulate the cells in the wound or tissue to heal with little or no scar formation relative to a control.

C. Scaffolding

Another embodiment provides a substrate or scaffold containing the disclosed acellularized biomaterial. The substrate or scaffold can be used to produce specific three dimensional constructs containing predetermined cells or tissue types. For example, a substrate or scaffold containing acellularized biomaterial specific for inducing the production of arterial tissue can be used to produce a three dimensional arterial construct. The construct can be produced by seeding the substrate or scaffold with totipotent or pluripotent cells which interact with the acellularized biomaterial and differentiate into arterial tissue. The substrate of scaffold directs the shape or form of the construct, for example, the construct can be tubular or planar.

Exemplary scaffolds or substrates are biodegradable or formed of biodegradable polymers. In other embodiments, the scaffolds or substrates are made of synthetic polymers including, but not limited to polyesters, polyurethanes, polyethers, polyamides, polyimides, or combinations thereof.

D. Methods of Treatment

The disclosed acellularized biomaterial can be used alone or in combination with autologous or heterologous cells including, but not limited to adult stem cells, embryonic stem cells, pluripotent cells, or somatic cells for promoting wound healing, for example by contacting a wound surface with acellularized biomaterial derived from one or more embryonic stem cells in an amount effective to promote or induce healing relative to a control. The cells can be added to the acellularized biomaterial before administration or after administration. One of skill in the art can readily ascertain "an amount effective to promote or induce healing relative to a control" using conventional techniques.

One embodiment provides a method for reducing scarring by contacting a wound with acellularized biomaterial derived from one or more differentiating embryonic stem cells in an amount effective to reduce scarring relative to a control. The acellularized biomaterial can be administered repeatedly as needed. In certain embodiments, the acellularized biomaterial is harvested from pluripotent cells induced to differentiate into the cells or tissue similar to the tissue to be treated. Thus, if the wound is in cardiac tissue, the acellularized biomaterial is harvested from pluripotent cells differentiating into cardiac cells or cardiac tissue.

Another embodiment provides a method for promoting tissue growth by contacting a tissue with acellularized biomaterial derived from one or more differentiating embryonic stem cells in an amount effective to promote endogenous tissue growth. In this embodiment, the acellularized biomaterial induces the cells of the tissue to participate in the healing process, for example by regenerating the tissue, producing growth factors or cytokines, dividing, or a combination thereof.

Still another embodiment provides a method for treating cardiac disease by contacting diseased or damaged cardiac tissue with acellularized biomaterial derived from embryonic stem cells undergoing cardiomyogenic differentiation. The acellularized biological material can be administered in an amount effective to promote or induce healing relative to a control.

Yet another embodiment provides a method for treating neural disease by contacting diseased or damaged neural tissue with acellularized biomaterial derived from embryonic stem cells undergoing neural differentiation.

Another embodiment provides a method for treating muscle disease by contacting diseased or damaged muscle tissue with acellularized biomaterial derived from embryonic stem cells undergoing myogenic differentiation.

Another embodiment provides a method for treating skin disease by contacting diseased or damaged skin with acellularized biomaterial derived from embryonic stem cells undergoing epithelial differentiation.

Another embodiment provides a method of inducing cartilage formation by administering acellularized biomaterial derived from embryonic stem cells undergoing differentiation to generate cartilage producing cells.

The disclosed acellularized biomaterial, alone or in combination with autologous or heterologous cells, for example pluripotent cells can be used to treat a variety of degenerative diseases. Representative disease that can be treated include, but are not limited to Alzheimer's disease, amyotrophic lateral sclerosis (ALS), atherosclerosis, cancer, diabetes, heart disease, inflammatory bowel disease (IBD), Parkinson's disease, prostatitis, osteoarthritis, and osteoporosis.

V. Devices

One embodiment provides a device for example a wound dressing. The wound dressing includes a backing having acellularized biomaterial derived from differentiating embryonic stem cells thereon. The wound dressing is applied to a wound so that the acellularized biomaterial contacts the wound and physically interacts with cells of the wound. The backing can be a fabric, felt, mesh, or polymer. The wound dressing optionally includes a moisture regulation layer, an absorbent layer, and adhesive flanking the acellularized biomaterial. The absorbent layer can be positioned between the backing and the acellularized biomaterial.

Another embodiment provides a stent having acellularized biomaterial derived from pluripotent cells, for example differentiating embryonic stem cells. The acellularized biomaterial can be on an external surface of the stent or an internal surface of the stent. Typically, the exterior surface of the stent is at least partially, preferably completely coated with the acellularized biomaterial, for example, in an amount effective to reduce arterial scarring. Stents are known in the art, and the disclosed acellularized biomaterial is not limited to use with any one stent or class of stent.

It will be appreciated that the disclosed acellularized biomaterial can be used in combination with a variety of medical devices that are implanted into a patient, for example a human patient. The medical device is typically coated with acellularized biomaterial in amounts effective to reduce scarring, to facilitate tissue integration, or both relative to a control. Exemplary implanted medical devices include but are not limited to pace makers, orthopedic implants, drug delivery devices, catheters, biosensors, dental implants, prosthetics, screws, braces, and pins.

Another embodiment provides a kit. The kit includes acellularized biomaterial derived from differentiating pluripotent cells, for example embryonic stem cells. The acellularized biomaterial can be packaged individually and can include buffers, reagents, written directions, and an applicator for administering the device.

EXAMPLES

Methods and Materials
Cell Culture

Mouse embryonic stem cells (D3) were cultured on gelatin-coated dishes with Dulbecco's modified eagle medium, supplemented with 15% fetal bovine serum, 2 mM L-glutamine, non-essential amino acids, antibiotic/antimycotics, and 0.1 mM β-mercaptoethanol. To maintain the cells in their undifferentiated state, $10^3$ U/ml leukemia inhibitory factor (LIF) (ESGRO) was added to the culture. Cells were passaged every two to three days when they reached ~70% confluence. For this study, cells were used at passages 20-30. To initiate embryoid body culture, ESCs were trypsinized and removed from the gelatin-coated dishes. Four million cells were transferred to non-tissue culture treated Petri dishes (Day 0) and placed on orbital rotary shakers at 40 rpm. EBs were fed every other day with differentiation media not containing LIF.

Acellularization

Embryoid bodies were harvested at days 4, 7, and/or 10 of differentiation. Equal amounts of starting material (EBs) were distributed across microcentrifuge tubes. For mass retention analyses, each tube was weighed before addition of the sample. Control EBs were either rinsed in phosphate buffered saline (PBS) and stored in 4° C. for subsequent solubilization or kept in serum-free media at 37° C. for cell viability measurements. Treatment groups were centrifuged at 18,000 rcf for two minutes before addition of the reagent being tested. Samples were rotated in a LabQuake Rotisserie for the desired period of time, spun down at 18,000 rcf for two minutes, rinsed twice with PBS, and, if applicable, rotated in a second reagent for a given amount of time. At the end of the treatment, samples were centrifuged for two minutes at 18,000 rcf, and rinsed twice in PBS. Reagents tested were combinations of Triton X-100 (VWR) and Dnase (~2,000 Kunitz units/mg, Worthington Biochemical Corp.).

Scanning Electron Microscopy

Untreated EBs and acellular samples were fixed in gluteraldehyde (2.5% in 0.2M cacodylate buffer) and post-fixed in 1% $OsO_4$ (Electron Microscopy Sciences). Samples were rinsed three times in 0.2M cacodylate buffer and transferred into acetone immediately prior to drying in a critical point dryer (Quorum Technologies). Each sample was gold sputter coated for 90 seconds in a sputter coater and viewed using the Hitachi S800 Scanning Electron Microscope.

Cell Viability

Immediately after collection and treatment, untreated EBs and acellular samples were incubated in alamarBlue solution (10% alamarBlue in serum-free media) for three hours (Biosource). Fluorescent measurements were taken (ex: 545 nm, em: 590 nm) using a SpectraMax M2e plate reader; readings were normalized to values obtained for untreated EBs to obtain relative values of percent viability. Additionally, live/dead staining was performed to corroborate the quantitative alamarBlue data. Untreated and treated EBs were transferred into wells of a six-well dish and incubated. The samples were then imaged using a TE inverted fluorescent microscope to capture both green and red fluorescence.

Protein Quantification

Untreated EBs and acellular samples were solubilized using 6M guanidine hydrochloride (GuHCl). Total protein content was assessed using the bicinchoninic acid (BCA) assay kit (Pierce). Samples and standards created from known concentrations of bovine serum albumin (20-2000 µg/mL) were incubated in the BCA solution for 30 minutes at 37° C., and absorbance readings were taken at 562 nm on a SpectraMax M2e plate reader. Unknowns were fitted to the albumin standard curve to determine protein concentration.

DNA Quantification DNA content of treated and untreated samples was quantified using the Quant-iT™ PicoGreen® dsDNA Assay kit (Molecular Probes). Samples were solubilized using 6M GuHCl and added to 20×TE buffer (200 mM Tris-HCl, 20 mM EDTA, pH=7.5) and PicoGreen dye solutions. Fluorescent measurements of unknowns and calf thymus DNA standards were taken using a SpectraMax M2e plate reader (ex: 485 nm, em: 528 nm). Unknowns were fitted to standard curves to determine DNA content.

Mass Retention

Untreated and acellularized EBs were rinsed twice in $dH_2O$ and stored overnight at −80° C. Samples were then freeze-dried for 24 hours using a Labconco lyophilizer and weighed. Mass retention was recorded as the difference between averaged untreated EBs and acellular material. All samples were created from the same amount of starting material.

Histology and Immunohistochemistry (IHC)

EBs were harvested by allowing the cell clusters to settle to the bottom of a tube. EBs or acellular products were incubated in either methyl carnoy or formalin fixatives for 30 minutes and embedded in Histogel®. Samples were then processed for histological sectioning through a series of xylene and alcohol rinses and paraffin embedding. Each group was sectioned into 5 µm slices and de-paraffinized. Some samples were stained with hematoxylin and eosin (H&E) using an Leica Autostainer XL. Sections undergoing IHC were washed in xylene and 100% ethanol (EtOH) after de-paraffinization. Endogenous peroxidase activity was quenched using 0.75% hydrogen peroxide in 100% methanol, after which the samples were hydrated in graded ethanol series (100% EtOH-35% EtOH) and rinsed in phosphate-buffered saline (PBS, pH 7.3). Samples were incubated in 1% bovine serum albumin for 30 minutes before addition of the hyaluronan binding protein (HABR-B) and an overnight incubation at 4° C. The Vector Elite ABC kit was then used for color staining development prior to counterstaining in Gills #3 hematoxylin. Coverslips were mounted on each sample using aqueous mounting medium with anti-fading agents (Biomeda Corp.) and imaged using a Nikon 80i Upright Microscope and SPOT imaging software.

Immunofluorescence (IF)

Samples fixed in 10% formalin were prepared for staining as stated above. After deparaffinization, histological sections were permeabilized and blocked for 45 minutes using 2% goat serum (GS) and 0.05% Triton X-100. Samples were incubated with collagen IV, fibronectin, or laminin-1 primary antibodies (polyclonal rabbit) overnight at 4° C. (1:80 dilution), rinsed with PBS, and then incubated with FITC-conjugated goat anti-rabbit secondary antibody (1:100 dilution) before counterstaining using Hoechst. Finally, coverslips were mounted using an aqueous mounting medium with anti-fading agents (Biomeda Corp.) and imaged using a Nikon 80i Fluorescent Upright Microscope.

Example 1

Acellularization of Embryoid Bodies

Figure 1:
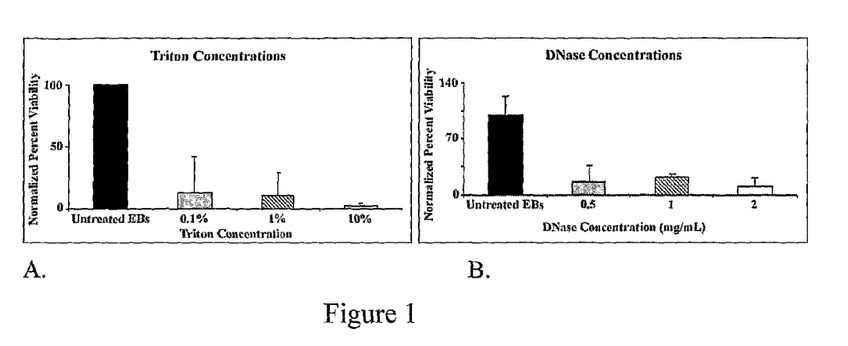
FIG. 1 shows bar graphs of normalized cell viability of embryoid bodies versus Triton X-100 concentration (A) or DNase concentration (B).
Figure 2:
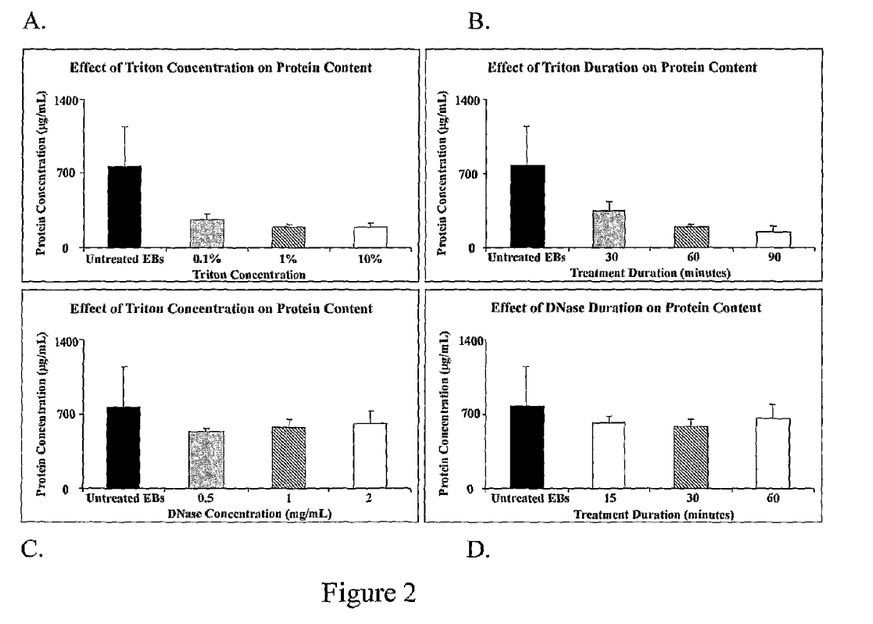
FIG. 2 shows bar graphs of protein concentration of embryoid bodies versus Triton X-100 concentration (A); Triton X duration (B); DNase concentration (C); and DNase duration (D).

Acellularization experiments were performed for variations in concentration and treatment time for Triton X-100 and DNase. Triton and DNase were evaluated for concentration optimizations using cell viability as a protocol efficiency indicator (FIGS. 1A and B). Viability was significantly inhibited in all cases, with no significant differences between each group.

Triton and DNase concentrations as well as treatment times were also evaluated via total protein content (FIGS. 2A-D). While protein content was retained in each experimental group, there were no significant differences within the Triton concentrations, the DNase concentrations, or the DNase treatment times. Within the Triton treatment times analyzed, a 30-minute period retained significantly more protein than both the 60- and 90-minute durations.

Figure 3:
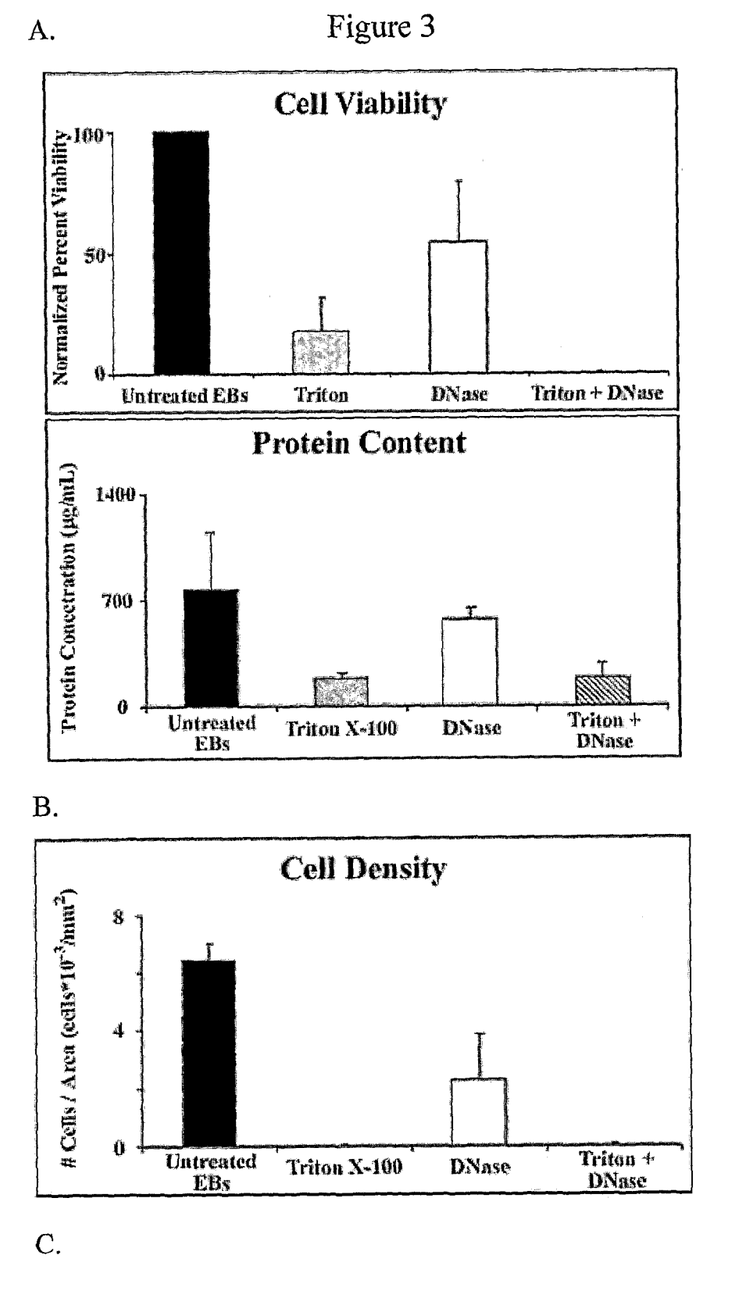
FIG. 3 shows bar graphs of normalized cell viability versus embryoid bodies treated with Triton X 100, DNase, or both (A); protein concentration of embryoid bodies treated with Triton X 100, DNase, or both (B); and cell density of embryoid bodies treated with Triton X 100, DNase, or both (C).

Finally, the combination of reagents was analyzed by evaluating cell viability, total protein content, and cell density when using Triton only, DNase only, and a combination of Triton and DNase (FIG. 3A-C). The Hoechst staining showed that nuclei were distinct in the untreated EBs, while all treatment groups showed either diffuse or absent nuclear staining. Images of Triton alone and DNase alone indicated that some nuclear material was present, although not as distinct as untreated samples, while little DNA signal was left when a combination of Triton and DNase was used. Quantification of cell nuclei further supported the use of Triton and DNase together for efficient cell removal. Additionally, cell viability data indicated the some viability remained in the Triton alone and DNase alone samples, while it was reduced below the assay detection limits for the combination of reagents. Protein content was also found to be retained in all samples.

Figure 4:
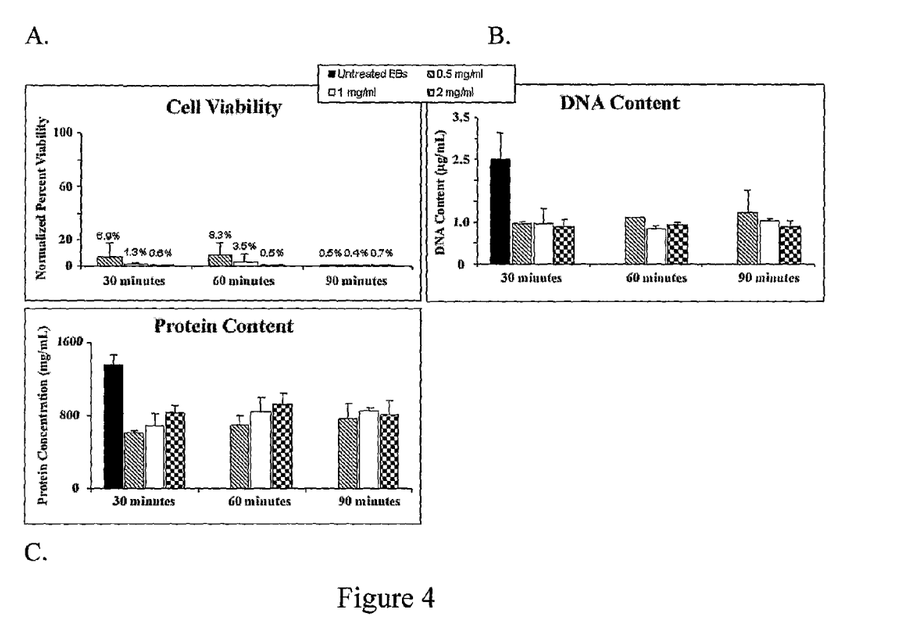
FIG. 4 shows bar graphs of normalized percent viability versus duration of treatment of embryoid bodies with DNase combined with Triton X 100 (A); DNA content versus time (B); and protein content versus time (C).

The optimized protocol using Triton and DNase together was further investigated through variations in DNase treatment times and concentrations, neither of which made a significant difference with viability, total protein content, or DNA content (FIG. 4A-C). DNase was mixed with 1% Triton, but this change in procedure made no significant difference in improving the existing protocol, in which Triton and DNase are used sequentially. Peracetic acid was investigated as an additional or alternative treatment, but was not found to significantly improve the efficiency of the Triton/DNase protocol. Additionally, EBs were cultured using ascorbic acid as an attempt to enhance quantity and protein content of the final acellular product (data not shown).

Example 2

Histology

H&E-stained sections of untreated and treated EBs showed the agglomeration of individual EBs after acellularization. While the EBs appeared to take on a more differentiated morphology, the acellular material showed little change over the course of differentiation. Individual cells were clearly present in the untreated EBs, while distinct nuclei were no longer observed in the acellular material.

Scanning electron micrographs at various magnifications display the surface detail of untreated EBs, as well as the surface and cross-section of acellular EBs. Images of the cross-section showed the porous nature of the product's interior, while comparisons between the acellular and untreated surfaces indicated that the acellularization procedure removed or destroyed individual cells and created one relatively uniform and flat material.

Example 3

Acellularization Protocol Analysis: Protein, DNA, and Mass Quantification

Figure 5:
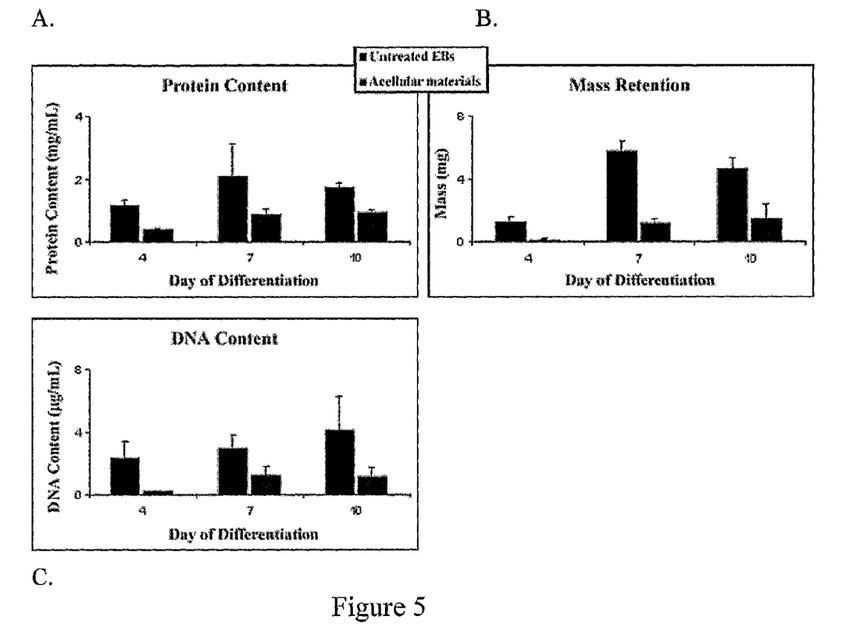
FIG. 5 shows bar graphs of protein concentration versus day of differentiation (A); mass versus day of differentiation (B); and DNA content versus day of differentiation (C) of embryoid bodies.

Once it was established that a combination of Triton and DNase was most efficient in acellularizing the EBs, analysis on total protein content, DNA content, and mass retention over the course of differentiation was performed on the final protocol (FIG. 5A-C). Protein content was maintained at days 4, 7, and 10. Additionally, DNA content was significantly reduced at each time point, with almost no remaining DNA left at day 4 and slightly more at days 7 and 10. Finally, mass was retained at days 7 and 10, suggesting that some material was left after the extraction process.

Example 4

Cell Viability and Component Retention

Figure 6:
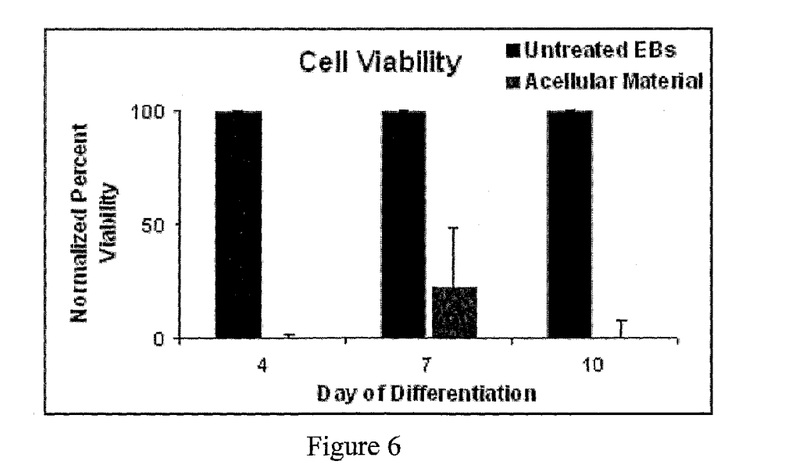
FIG. 6 shows a bar graph of normalized cell viability versus day of differentiation.

Cell viability over the course of differentiation was analyzed using both quantitative and visual assays. The Live/Dead assay showed all live and no dead cells over the course of differentiation of untreated EBs. Acellular material showed mostly dead cells at days 4 and 10, with some live at day 7. This visual information was corroborated with the quantitative alamarBlue data, which showed viability below the levels of the assay's detection limit at days 4 and 10, and ~25% viability at day 7 (FIG. 6).

Initial studies to analyze which extracellular matrix components remained after the extraction process were performed using immunostaining. Collagen IV, laminin-1, and hyaluronan content was visualized in untreated EBs and acellular material. All three components were spatially spread around the untreated EBs. Hyaluronan seemed to localize at areas of lower cell density. Importantly, significant amounts of the individual proteins or glycosaminoglycans were maintained through acellularization and were found to be present throughout the final product.

Example 5

Cardiomyogenic Differentiation of ES Cells

Mouse ES cells are typically induced to differentiate via embryoid body (EB) formation by either the hanging drop technique or static suspension culture, although both methods have inherent limitations. While EBs produced by hanging drops are more uniform in size, shape and subsequent differentiation behavior, the need to keep individual drops physically separated prevents efficient production of a large number of EBs. Static suspension cultures, on the other hand, can be easily initiated from a cell suspension, but the resulting EBs vary widely in size, shape and differentiation. In addition, during static suspension, EBs often prematurely attach to the surface of the Petri dish, reducing the overall yield of differentiated cells, unless low-adhesion surface coatings are employed. It was recently discovered that by simply placing suspension EB cultures in untreated bacteriological dishes on a rotary plate during EB formation, the homogeneity of EB size and shape can be significantly improved as well as the overall yield of EBs and the reproducibility of differentiation.

Figure 7:
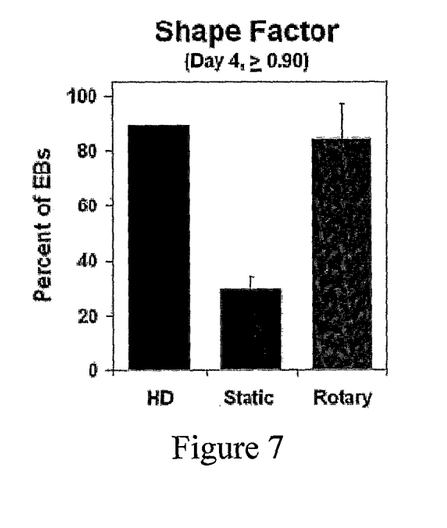
FIG. 7 shows a bar graph of embryoid body formation using rotary or static culture procedures.

Mouse ES cells (D3 line) were cultured under feeder-free growth conditions in the presence of LIF (103 U/ml). To initiate differentiation, LIF was removed from the culture media and EBs were placed in hanging drops on the lids of Petri dishes (600 cells/15 µl drop) or in suspension culture ($4 \times 10^5$ cells/ml; 10 ml/100 mm dish). Rotary suspensions were achieved by placing suspension dishes on a rotary plate (Barnstead Thermolyne) within a humidified $CO_2$ incubator. After 4 days of differentiation, phase contrast images of EBs formed by the different methods were obtained and the cross-sectional area and shape factor (defined as the minor axis divided by the major axis) of individual EBs were measured with ImageJ software. Molphometric analysis indicated that the rotary cultures were similar in size and shape to the hanging drop EBs, whereas the static cultures were noticeably irregular. There was also a greater number of EBs produced in rotary cultures than in static cultures inoculated with an equivalent number of cells (FIG. 7).

Figure 8:
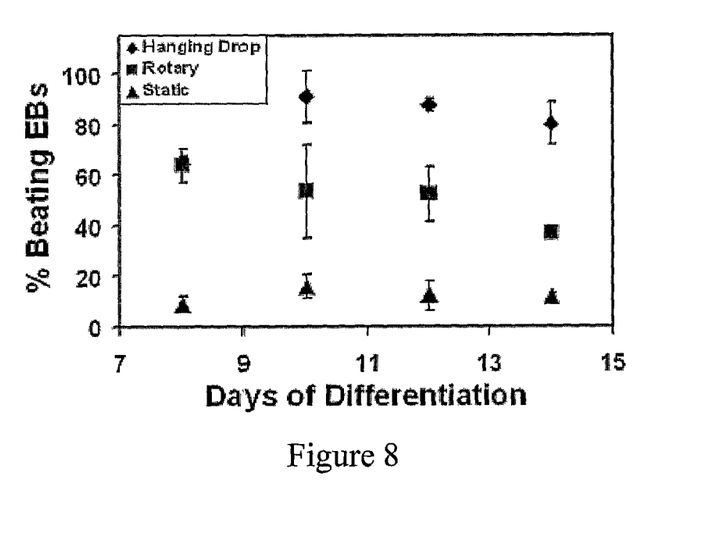
FIG. 8 shows a scatter plot of beating embryoid bodies produced using static or rotary culture procedures.

Cardiogenesis of the EBs formed by the different methods was examined by counting the percentage of beating EBs upon plating and assessing the gene expression profile of the cells during the time course of differentiation. One day after plating (day 8 of differentiation), the percentage of EBs that contained at least one beating foci was about 60% for both hanging drop and rotary cultures, whereas fewer than 10% of the static EBs exhibited contractile areas (FIG. 8). While the percentage of contractile hanging drop EBs increased slightly over time (to ~80%), the number of beating rotary EBs remained relatively constant (~50%), but the contractile areas increased in size and contracted more vigorously. In addition, the number of beating foci within EBs from rotary cultures appeared to increase over the time course examined, but this was not quantifiable due to difficulties in discriminating between distinct and merged foci within individual EB outgrowths.

Figure 9:
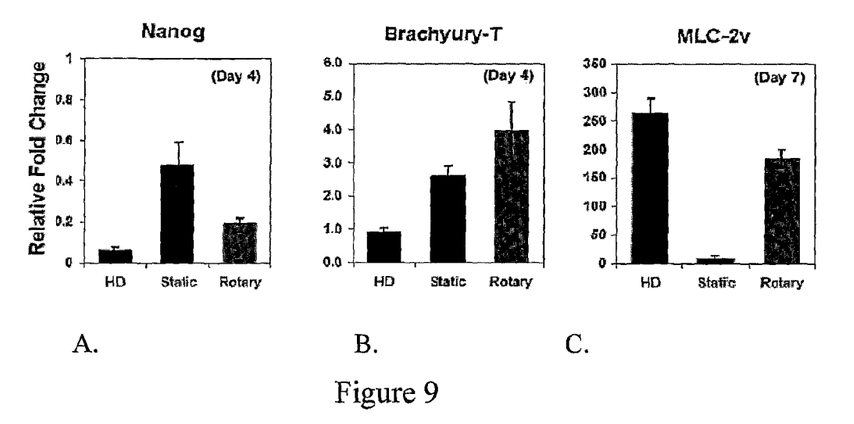
FIG. 9 shows bar graphs indicating fold increase in Nanog (A), Brachyury T (B), or MLC-2v (C) expression of embryoid bodies produced using static or rotary culture procedures.

Semi-quantitative real-time PCR analysis indicated a more pronounced decrease in Nanog expression (a pluripotent stem cell marker) in hanging drop and rotary EBs than in static suspensions (FIG. 9A), suggesting more efficient induction of differentiation. Rotary EBs exhibited a significant increase in mesoderm formation, based on Brachyury-T expression, after 4 days compared to hanging drop and static suspension EBs, although the weaker levels of Brachyury T in hanging drops at 4 days could be related to the rapidly transient nature of its expression during differentiation (FIG. 9B). Cardiomyocyte gene expression, based on MLC-2v expression, was also significantly greater in both hanging drop and rotary EBs at day 7 of differentiation than in static suspension EBs (FIG. 9C). Thus, gene expression results correlated with the observed differentiation and contractile activity of the plated EBs, suggesting that the rotary culture method is an effective means of promoting cardiomyogenic differentiation from ES cells with an overall greater yield of EBs than either hanging drop or suspension methods.

Example 6

Acellularized Biomaterial for Cardiac Tissue Repair

Mouse ES cells were cultured and differentiated via EB formation as described above. After 4 days of differentiation, the resulting EBs were harvested and subjected to detergent and/or enzymatic treatments in an attempt to extract cellular material and retain the residual insoluble ECM. EB samples were treated with Triton X-100 (0.1% or 1% w/v) or DNase (1 mg/ml) solutions for 30 minutes. The resulting material was analyzed histologically by Hoechst staining. Mass retention was calculated from pre- and post-treatment values and cell viability was measured with the Alamar Blue assay (Biosource). Acellularization with Triton X-100 induced the individual EBs to aggregate within minutes, forming a viscous mass of contiguous material readily retrievable by centrifugation. Histology indicated Triton X treatment (0.1%) alone disrupted the normal distinct, round cell nuclei morphology to yield a fibroporous acellular material. Mass calculations of the starting and final material indicated that a majority of the mass was retained following acellularization (~70-80%), and the percentage of mass retained decreased with increasing concentration of Triton X-100. Cell viability was significantly decreased by DNase treatment alone and completely abrogated by Triton X-100 treatment, indicating successful acellularization of the EBs. Similar results have also been obtained from acellularized EBs after 7 days of differentiation, indicating that the timing of cell extraction can be selectively controlled.

In summary, the aforementioned studies have established that acellularization of EBs by solvent extraction methods yields a novel biomaterial derived from ES cells during the course of in vitro differentiation.

Example 7

Cardiac Grafting of Acellularized Materials

Acellularized EB material was grafted onto the epicardial surface of infarcted hearts of male CDF rats immediately after being subjected to a left coronary artery ligation. Acellular materials (~2×2 mm) were affixed to the hearts with one drop (<100 µl) of fibrin glue. Hearts were retrieved 1 or 13 days later, fixed and stained with hematoxylin and eosin. After 1 day, the material was retained on the surface of the heart adjacent to the developing infarcted tissue and was largely free of any cell nuclei. By 13 days, the acellular material was no longer readily discernible and significant differences were apparent in the healing response, wall thickness and chamber size for infarcted hearts with the acellular material, compared to untreated controls. These results show that acellular ECM from ES cells can be grafted onto infarcted rat hearts and alter the course of normal ventricular remodeling after myocardial infarction.

Unless defined otherwise, all technical and scientific terms used herein have the same meanings as commonly understood by one of skill in the art to which the disclosed invention belongs. Publications cited herein and the materials for which they are cited are specifically incorporated by reference where permissible.

Those skilled in the art will recognize, or be able to ascertain using no more than routine experimentation, many equivalents to the specific embodiments of the invention described herein. Such equivalents are intended to be encompassed by the following claims.

We claim:

1. A composition comprising acellularized embryoid-body-biomaterial comprising a combination of paracrine factors produced by one or more differentiating embryoid bodies in an amount effective to promote or induce wound healing relative to a control.

2. The composition of claim 1, wherein the one or more differentiating embryoid bodies undergo cardiac differentiation, neural differentiation, myogenic differentiation, epidermal differentiation, or a combination thereof.

3. The composition of claim 1, wherein the one or more embryoid bodies comprises a heterologous nucleic acid.

4. A pharmaceutical composition comprising acellularized embryoid-body-biomaterial produced by a process comprising acellularizing one or more in vitro differentiating embryoid bodies wherein the acellularized embryoid-body-biomaterial comprises a combination of paracrine factors produced by differentiating embryoid bodies in an amount effective to promote or induce wound healing.

5. The pharmaceutical composition of claim 4, further comprising an excipient.

6. A composition comprising acellularized embryoid-body-biomaterial produced by a process comprising acellularizing in vitro differentiating embryoid bodies, wherein the acellularized embryoid-body-biomaterial comprises an effective amount of a combination of paracrine factors produced by the differentiating embryoid bodies to alter the microenvironment of a wound or damaged tissue to induce or facilitate regenerative tissue repair in vivo.

7. A medical device comprising acellularized biomaterial according to claim 1 or 6.

8. The medical device of claim 7, wherein the device is selected from the group consisting of a wound dressing, stent, orthotic, suture, implant, catheter, rod, pin, delivery vehicle, and brace.

9. A kit comprising acellularized biomaterial according to claim 1, 4, or 6.

10. The kit of claim 9, further comprising one or more pluripotent cells.

11. The kit of claim 9, wherein the acellularized biomaterial is tissue specific.

12. The composition of claim 1, wherein the acellularized embryoid-body-biomaterial is non-human.

* * * * *